United States Patent [19]

Lagow

[11] Patent Number: 4,788,350
[45] Date of Patent: Nov. 29, 1988

[54] SPHERICAL PERFLUOROETHERS

[76] Inventor: Richard J. Lagow, 100 Navajo Trail, Georgetown, Tex. 78628

[21] Appl. No.: 91,659

[22] Filed: Sep. 1, 1987

[51] Int. Cl.$^4$ ............................................. C07C 43/12
[52] U.S. Cl. .................................... 568/677; 252/54; 228/56.3; 436/62
[58] Field of Search ........................................ 568/677

[56] References Cited

U.S. PATENT DOCUMENTS 2,611,787 9/1952 Holm .
4,113,435 9/1978 Lagow et al. ...................... 568/677

Primary Examiner—Howard T. Mars
Attorney, Agent, or Firm—Hamilton, Brook, Smith & Reynolds

[57] ABSTRACT

Perfluoroethers having a spherical shape are described. The perfluoroethers can be represented by the formula

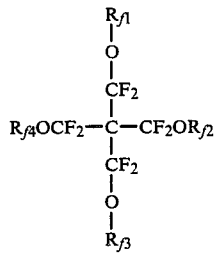

wherein $R_{f1}$, $R_{f2}$, $R_{f3}$ and $R_{f4}$ are the same or different and are selected from short, straight or branched chain perfluoroalkyl or perfluoroether groups. The perfluoropolyethers are designed to act like "molecular ball bearings" and have high thermal stability and lubrication properties. They are useful as stable fluids, heat transfer fluids, vapor phase soldering fluids and oxygen carriers.

6 Claims, No Drawings

SPHERICAL PERFLUOROETHERS

BACKGROUND

Fluorocarbons and related compounds such as fluorocarbon amines and ethers have become an essential component of many 'high technology' industries. The unique combination of properties such as resistance to chemical oxidation, thermal stability, low toxicity and non-flammability have assured the use of such materials in situations where a particular need is of such importance that the relatively high cost is justified.

Several types of fluorocarbon fluids have found specialized uses as coolants and insulators in high voltage equipment, immersion media for leak testing, and heat transfer agents in vapor phase soldering processes. Preparation, Properties and Industrial Applications of Organofluorine Compounds (ed. R. E. Banks) Wiley and Sons, NY, 1982. They are used as vacuum pump fluids where their chemical stability allows a very clean vacuum even where hostile chemical and physical conditions are involved. Caporiccio, G., et al., *Ind. Eng. Chem. Prod. Res. Dev.* 21, 515–519 (1982).

Several commercially available polyether fluids are made by the telomerization of hexafluoropropylene oxide. These materials are produced by the photo-oxidation of liquid hexafluoropropylene to yield polyperoxides, $-(C_3F_6O)_m-(C_3F_6OO)_n-$ which are heated to destroy the peroxide linkages. The resultant polymers are end capped by reaction with elemental fluorine. The material is then separated into various fractions by distillation. Sianesi, D., et al., *Chim. Ind.* (Milan) 1973, 55(2), 208–221.

Fluorocarbon polyethers have been made by several routes by direct fluorination. The direct reaction of polyethers such as poly(ethylene glycol) (Gerhardt, G. and Lagow, R. J., *J. Org. Chem.* 43, 4505, (1978)) poly(propylene oxide) and poly(methylene oxide) (Gerhardt, G. and Lagow, R. J., Chem. Soc. Perkin Trans. 1 1321 (1981)) gave corresponding fluorocarbon polyethers. The fluorination of copolymers of hexafluoroacetone and either ethylene oxide, propylene oxide or trimethylene oxide (Persico, D. F. and Lagow, R. J., *Macromolecules* 18, 1383 (1985)) yielded perfluoropolyethers with a branched structure. Finally the action of sulfur tetrafluoride on polyesters (Persico, D. F. and Lagow, R. J., Makromol. Chem. Rapid Commun. 6, 85 (1985)) also gives fluorocarbon polyethers of various structures.

SUMMARY OF THE INVENTION

This invention pertains to perfluorinated "spherical" ethers and to methods of synthesizing these compounds. The perfluoroethers of this invention are represented by the formula:

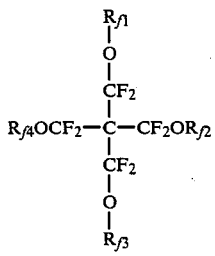

wherein $R_{f1}$, $R_{f2}$, $R_{f3}$ and $R_{f4}$ are the same or different and are selected from short, straight or branched chain perfluoroalkyl or perfluoroether groups. For example, $R_{f1}-R_{f4}$ can be selected from $CF_3$, $C_2F_5$, $C_3F_7$, $C_4F_9$, $C_5F_{11}$, $C_3F_7$, $C_2F_6$, $C_2F_4OCF_3$, $CF_2OC_4F_9$, $CF_2OC_5F_{11}$ and $CF_2OC_2F_4OCF_3$. Preferred ethers are represented by the formula:

wherein $R_f$ is defined as above.

The perfluoroethers of this invention are synthesized by direct elemental fluorination of corresponding hydrocarbon ethers under controlled conditions. The perfluoroethers are useful lubricants, heat exchange fluids, vapor phase soldering fluids and oxygen carriers.

DETAILED DESCRIPTION OF THE INVENTION

The perfluoroethers of this invention are represented by the formula:

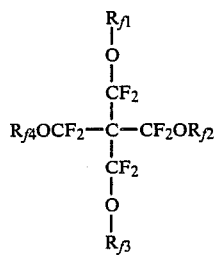

wherein $R_{f1}$, $R_{f2}$, $R_{f3}$ and $R_{f4}$ are the same or different and are selected from short, straight or branched chain perfluoroalkyl or perfluoroether groups. For example, $R_{f1}-R_{f4}$ can be selected from $CF_3$, $C_2F_5$, $C_3F_7$, $C_4F_9$, $C_5F_{11}$, $C_3F_7$, $C_2F_6$, $C_2F_4OCF_3$, $CF_2OC_4F_9$, $CF_2OC_5F_{11}$ and $CF_2OC_2F_4OCF_3$. Preferred ethers are represented by the formula:

wherein $R_f$ is defined as above.

The perfluoroethers of this invention are produced by the direct fluorination technique of Lagow and Margrave, *Prog. of Org. Chem.* 26, 161: (1979). The corresponding hydrocarbon ether is selected or synthesized (for example, by the syntheses described below). The hydrocarbon ethers are represented generally by the formula:

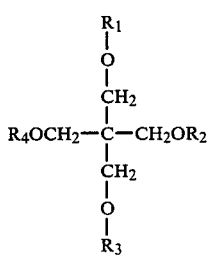

wherein $R_1$, $R_2$, $R_3$ and $R_4$ are the same or different and are selected from short, straight or branched chain alkyl or alkyl ether groups.

The starting material is placed in a fluorine reactor such as the reactor described below. Preferably the reactor is designed so that low vapor pressure starting materials can be coated onto an inert support. The support can be in a powder form to maximize the surface area exposed to the fluorine and evenly distribute the material throughout the reaction zone. When the mixture is not carefully distributed extensive degradation of the reaction and localized burning can occur. Copper turnings can be used as a support and heat sink, drawing the heat of reaction away from the reactants. The whole reactor can be placed inside an oven that can be heated or cooled as desired and provide better control over the temperature in the reaction zone.

The reactor is cooled and flushed with an inert gas such as helium or nitrogen after which the fluorine is initiated under controlled conditions. Typically, low fluorine concentrations between about one and about ten percent are used initially. The dilute fluorine is passed over the material to be fluorinated. As the fluorination reaction proceeds the fluorine concentration and flow rate of the gas are gradually increased until pure fluorine conditions are achieved and the ether is perfluorinated.

The best results are obtained when the fluorination is performed in the presence of a hydrogen fluoride scavenger such as sodium fluoride as described in U.S. patent application Ser. No. 924,198, entitled "Perfluorination of Ethers in the Presence of Hydrogen Fluoride Scavengers", filed Oct. 27, 1986, the teachings of which are incorporated herein. The presence of a hydrogen fluoride scavenger allows the use of more severe fluorination conditions in this direct fluorination procedure, that is, higher fluorine concentrations and faster rates of fluorine delivery can be used in the presence of a hydrogen fluoride scavenger than can be used in the absence of a scavenger. For example, initial fluorine levels of over 15% and up to 25% and fluorine flow rates of over 8 cc/min/gram of starting material can be used.

In addition, the yield and quality of the perfluoropolyether product is improved when fluorination is conducted in the presence of a hydrogen fluoride scavenger. The scavenger is believed to prevent the formation of ether-HF acid base complexes during the fluorination reaction.

Fluorination in the presence of a hydrogen fluoride scavenger can be performed in several ways. In one mode, the hydrogen fluoride scavenger (in powdered or pellet form) is mixed with the ether to be fluorinated. The blend is placed in a suitable fluorination reactor and fluorinated by exposure to gradually increasing concentrations of fluorine gas. In the preferred mode, the ether is coated onto the hydrogen scavenger and fluorinated in this form.

The perfluoroethers of this invention are useful as lubricants, heat exhange fluids, vapor phase soldering fluids, solvents and oxygen carriers. For example, the oils are useful as vacuum pump oils and oils for diffusion pumps. The more volatile are used to cool without corrosion electronic devices such as computers. The perfluoroethers are also useful as perfluorocarbon solvents, as oxygen carriers in biomedical applications and as oxygen carriers for organic oxidation reactions.

The invention is illustrated further by the following examples.

EXAMPLES

All of the ethers were synthesized by phase transfer catalyst conditions. Freedman, H. H. and Dubois, R. A. *Tetrahedron Lett.* (1975), 38, 325. Pentaerythritol, 1,1,1-tris(hydroxymethyl)ethane, dimethyl sulfate, diethyl sulfate, 1-bromopropane, 1-bromobutane, 1-bromobutane, and 2-chloroethyl ether were all used as received. A five fold excess of 50% sodium hydroxide over the alcohol, an excess of alkyl halide, and 5 mole % of phase transfer catalyst methyltrialkyl ($C_8$-$C_{10}$)-ammonium chloride ("Adogen" 464, Aldrich Chem. Co) were stirred at 70° C., generally overnight. The ethers were fractionally distilled and stored over 4A molecular sieve until use.

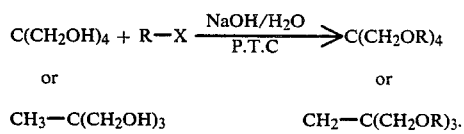

For the fluorination of the hydrocarbon ethers, a 9 inch (i.d.) by 2 inch tall cylindrical reactor was used. The reactor was fitted with ⅜ inch inlet and outlet and a thermocouple probe. A Viton ® O-ring provided a gas tight seal. The reactor was held in an insulated oven equipped with a cryogenic controller and liquid nitrogen cooling. A heating coil and fan provided the elevated temperatures at the end of the reactions.

In a typical fluorination reaction 5 to 10 grams of the ether starting material was mixed with 100 grams of dry #120 mesh sodium fluoride powder. The mixture was stirred and shaken until it appeared homogenous. The mixture was then distributed on tightly packed copper turnings in the reactor cavity. The reactor assembly was then connected to the flourination system, cooled to −50° C. and purged overnight with a 60 cc $\text{min}^{-1}$ flow of helium. Flourination conditions are outlined in Table 1.

TABLE 1

$$C(CH_2OR_H)_4 \xrightarrow{F_2/He} C(CF_2OR_F)_4 + HF$$

| | Fluorination Conditions | | |
|---|---|---|---|
| He ($cm^3 min^{-1}$) | $F_2$ ($cm^2 min^{-1}$) | Temperature (°C.) | Time (hours) |
| 50 | 0.5 | −80 | 24 |
| 50 | 1 | −80 | 24 |
| 50 | 2 | −80 | 24 |
| 50 | 4 | −80 | 24 |
| 20 | 4 | −80 | 24 |
| 10 | 4 | −80 | 24 |
| 0 | 4 | −80 | 24 |
| 0 | 2 | −50 | 24 |
| 0 | 2 | −10 | 24 |
| 0 | 2 | 25 | 24 |
| 0 | 2 | 60 | 18 |
| 60 | 0 | 150 | 24 |

After the reaction with fluorine was complete, the compounds were purged from the reactor by heating the oven to 200° C. and turning the helium flow to 100 cc $\text{min}^{-1}$. The products were caught in a Kel-$F^R$ trap held at −80° C. with a dry ice—acetone slush. One half milliliter of hexamethyl disilazane was added to react with any acidic fluorides in the liquid. The liquid was then fractionally distilled. Further purification was done on a Hewlett Packard 5880A gas chromatograph.

The columns used were ¼ inch by 10 foot stainless steel packed with either 25% OV −210 or 25% Fomblin Z on Chromosorb A (60/80 mesh).

PHYSICAL MEASUREMENTS

Elemental analyses were performed by E+R Micro analytical Laboratory, Inc., Corona, NY. Infrared analyses were done on a Biorad Digilabs FTS-40 spectrometer using a thin film on KBr windows. Fluorine nmr spectra were recorded on a Varian EM-390 spectrometer operating at 84.6 MHz. Chemical ionization mass spectra were performed on a Finnigan-MAT TSQ-70 mass spectrometer.

EXAMPLE 1

Perfluoro-4,4-Bis(Methoxymethyl)-2,6-Dioxaheptane

A 5.04 gram sample of the hydrocarbon ether was fluorinated as described above. The crude product was separated on a vacuum line first, using traps held at −45° C., −78° C., and −196° C. The majority of the product stopped in the −45° C. trap. The final purification was done on the 25% Fomblin Z column held at 100° C. isothermal. The crude product was shown to be 80% pure with no one major impurity. The final weight of product was 3.5 grams corresponding to a yield of 38%.

The fluorinated ether is a colorless liquid with a boiling freezing point of −87° C. Elemental analysis of the compound: calculated for C 19.56%, F 68.66%; found C 19.34%, F 68.84%. Chemical ionization mass spectrometry gives m/e 552 as the largest peak.

EXAMPLE 2

Perfluoro-5,5-Bis(Ethoxymethyl)-3,7-Dioxanonane

A 5.97 gram sample of the starting material was prepared as previously described. The crude product was vacuum distilled at 40 mm Hg, boiling at 65°-70° C. Final purification was done by gas chromatography using the 25% Fomblin Z column at 185° C. isothermal. The final weight of product was 4.18 grams corresponding to a yield of 25%. The fluoroether is a clear liquid with a boiling poing of 170° C. and a freezing point of −60° C. Elemental analysis of the compound: calculated for C 20.76%, F 70.73%; found for C 20.44%, F 70.61%. Negative ion chemical ionization mass spectrometry showed the largest m/e to be 752.

EXAMPLE 3

Perfluoro-6,6-Bis(Propyloxymethyl)-4,8-Dioxaundecane 5.37 grams of hydrocarbon ether was loaded into the reactor and fluorinated using the conditions essentially outlined in Table 1. The crude product was first vacuum distilled at a pressure of 15 mm Hg, boiling at 185°-190° C. The final purification was done on the 25% Fomblin column at 185° C. A final weight of 5.32 grams gave a yield of 31%. The clear liquid has a boiling point of 232° C. and a melting point of −54° C. Elemental analysis of the product corresponded with calculated values.

EXAMPLE 4

Perfluoro-7,7-Bis(2-Methoxyethoxymethyl)-2,5,9,12-Tetraoxatridecane 10.03 grams of starting ether was loaded into the reactor as previously described. After purging the fluorination was started. The contents of the −80° C. trap was fractionally distilled (bp$_{10}$ 95° C.). Final purification was done on the 25% OV-210 column at 185° C. The final weight of product was 8.42 grams for a yield of 30%. Elemental analysis of the product corresponded with calculated values. Mass spectrometry gave m/e 1016.

EXAMPLE 5

Perfluoro-7,7-Bis(Butyloxymethyl)-5,9-Dioxatridecane

A sample of 10.21 grams of starting material was fluorinated essentially as outlined in Table 1. The contents of the trap was fractionally distilled (bp$_{10}$ 126° C.). 12.09 grams of heavy liquid was collected giving a 37% yield for the reaction. Elemental analysis for the compound corresponded with calculated values. A peak at m/e 1152 appeared in the mass spectrum.

EXAMPLE 6

Perfluoro-8,8-Bis(Pentyloxy)-6,10-Dioxapentadecane 11.71 grams of hydrocarbon ether was loaded into the reactor and fluorinated using the conditions essentially as outlined in Table 1. Fractional vacuum distillation of the trap contents yielded 3.20 grams of clear heavy liquid (bp$_{10}$ 150° C.). The yield of fluorinated ether was 8.4%. Elemental analysis of the product corresponded with calculated values. Mass spectrometry showed m/e 1352.

EXAMPLE 7

Perfluoro-7Methyl-(2-Methoxyethoxymethyl)-2,5,9,12-Tetraoxatridecane 6.00 grams of staring material ether was fluorinated as described above. Vacuum fractional distillation of the trap contents followed by chromatography on the 25% (bp$_{10}$OV-210 column at 185° C. isothermal gave 3.57 grams of material 92° C.). Elemental analysis of clear liquid corresponded with calculated values. Mass spectrometry gave m/e 834.

EXAMPLE 8

Perfluoro-7-Methyl-7-(Butyloxymethyl)-5,9-Dioxatridecane

A sample of 4.55 grams of the ether was subjected to the fluorination conditions essentially as described in Table 9. After completion of the fluorination, the contents of the trap were fractionally distilled (bp$_{10}$ 105° C.). 5.32 grams of clear heavy liquid was collected. The overall yield of the reaction was 36%. Elemental analysis of the product corresponded with calculated values. A m/e of 936 appeared in the mass spectrum.

EXAMPLE 9

Perfluoro-8Methyl-8(Pentyloxymethyl)-6,10-Dioxapentadecane 73

4.50 grams of starting material was fluorinated as described. After purging the reactor at 200° C. with a 100 cc min$^{-1}$ flow of helium into the Kel-F$^R$ trap. Fractional vacuum distillation of the contents yielded (bp$_{10}$ 130° C.) 1.36 grams of heavy clear liquid. The overall yield of the reaction was 9.2%. Elemental analysis of the material corresponded with calculated values. A peak at m/d 1086 appeared in the mass spectrum.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. Perfluoroethers of the formula:

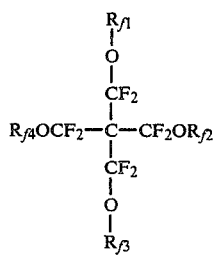

-continued

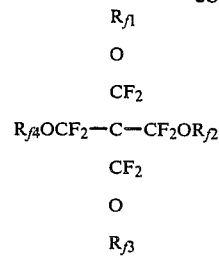

wherein $R_{f1}$, $R_{f2}$, $R_{f3}$ and $R_{f4}$ are the same of different and are selected from short, straight or branched chain perfluoroalkyl or perfluoroether groups.

2. Perfluoroethers of claim 1, wherein $Rf_1$, $Rf_2$, $Rf_3$ and $Rf_4$ are same or different and are selected from $CF_3C_2F_5$, $C_3F_7$, $C_4F_9$, $C_5F_{11}$, $C_3F_7$, $C_2F_6$, $C_2F_4OCF_3$, $CF_2OC_2F_9$, $CF_2OC_5F_{11}$ and $CF_2OC_2F_4OCF_3$.

3. Perfluoroethers of the formula:

$$C-(CF_2-O-R_f)_4$$

wherein $R_f$ is selected from $CF_3$, $C_3F_7$, $C_4F_9$, $C_5F_{11}$, $C_3F_7$, $C_2F_6$, $C_2F_4OCF_3$, $CF_2OC_4F_9$, $CF_2OC_5F_{11}$ and $CF_2OC_2F_4OCF_3$.

4. Perfluoro-(pentaerythrityl-tetramethylether).
5. Perfluoro-(pentaerythrityl tetra-t-butyl ether).
6. Perfluoro-(pentaerythrityl-tetraethyl ether).

* * * * *

UNITED STATES PATENT AND TRADEMARK OFFICE
CERTIFICATE OF CORRECTION

PATENT NO. : 4,788,350

DATED : November 29, 1988

INVENTOR(S) : Richard J. Lagow

It is certified that error appears in the above—identified patent and that said Letters Patent is hereby corrected as shown below:

Column 1, after the title, insert

Government Support
 This invention was made with Government Support under Grant AFOSR-87-0016, awarded by the Air Force and Grant NAG3-602, awarded by the National Aeronautics and Space Administration. The Government has certain rights in this invention.---

Column 4, line 37, delete "flourination" and insert ---fluorination---.

Column 4, line 39, delete "Flourination" and insert ---Fluorination---.

Column 4, line 43, the equation should appear above the Table 1.

In the Claims
 Column 8, line 2, the formula should be deleted.

Column 8, line 13, delete "of" and insert ---or---.

Claim 1, column 8, line 18, delete "$CF_3C_2F_5$" and insert ---$CF_3$, $C_2F_5$---.

Signed and Sealed this

Twenty-fifth Day of April, 1989

Attest:

DONALD J. QUIGG

Attesting Officer

Commissioner of Patents and Trademarks